(12) United States Patent
Quandt et al.

(10) Patent No.: US 6,384,304 B1
(45) Date of Patent: May 7, 2002

(54) CONDITIONAL STERILITY IN WHEAT

(75) Inventors: Jürgen Quandt, Saskatoon (CA); Klaus Bartsch, Königstein; Nathalie Knittel, Frankfurt, both of (DE)

(73) Assignee: Plant Genetic Systems N.V., Gent (BE)

( * ) Notice: Subject to any disclaimer, the term of this patent is extended or adjusted under 35 U.S.C. 154(b) by 0 days.

(21) Appl. No.: 09/418,817

(22) Filed: Oct. 15, 1999

(51) Int. Cl.$^7$ .................. C12N 15/82; C12N 15/31; C12N 5/04; A01H 5/00; A01H 1/02

(52) U.S. Cl. ............... 800/320.3; 800/271; 800/274; 800/278; 800/287; 800/288; 800/300; 800/303; 435/418; 435/419; 435/468

(58) Field of Search ............... 800/320.3, 288, 800/300, 287, 274, 303, 271, 278; 435/418, 419, 468

(56) References Cited

U.S. PATENT DOCUMENTS

| | | |
|---|---|---|
| 5,633,441 A | 5/1997 | DeGreef et al. ............ 800/205 |
| 5,650,310 A | 7/1997 | Broer et al. ............ 435/172.3 |
| 5,668,297 A | 9/1997 | Broer et al. ............ 800/205 |
| 5,689,041 A | 11/1997 | Mariani et al. ............ 800/205 |
| 5,723,763 A | 3/1998 | Mariani et al. ............ 800/205 |
| 5,767,370 A | 6/1998 | Broer et al. ............ 800/205 |
| 5,767,371 A | 6/1998 | Broer et al. ............ 800/205 |
| 5,767,374 A | 6/1998 | DeGreef et al. ............ 800/205 |
| 5,792,929 A | 8/1998 | Mariani et al. ............ 800/205 |
| 5,981,189 A * | 11/1999 | Chan et al. ............ 435/6 |
| 6,177,616 B1 * | 1/2001 | Bartsch et al. ............ 800/303 |

FOREIGN PATENT DOCUMENTS

| | | |
|---|---|---|
| EP | 344029 | 11/1989 |
| WO | WO 98/13504 | 4/1998 |
| WO | WO 98/27201 | 6/1998 |
| WO | WO 98/39462 | 9/1998 |

OTHER PUBLICATIONS

Kriete G. et al., "Male sterility in transgenic tobacco plants induced by tapetum–specific deacetylation of the externally appliec non–toxic comound N–acetyl–L–phosphinothricin." 1996, The Plant Journal, vol. 9, pp. 809–818.*

"The development of a nuclear male sterility system in wheat. Expression of the barnase gene under the control of tapetum specific promoters"; DeBlock et al., 1997, Theor. Genet. 95: 125–131.

* cited by examiner

*Primary Examiner*—David T. Fox
(74) *Attorney, Agent, or Firm*—Frommer Lawrence & Haug LLP

(57) ABSTRACT

The invention relates to the use of a deacetylase coding sequence for obtaining conditional sterility in wheat. The invention relates to vectors comprising a deacetylase coding sequence under control of promoters which direct stamen-selective expression in wheat, which are particularly suited for the production of wheat plants which can be made male-sterile upon application of an acetylated toxin.

26 Claims, 5 Drawing Sheets

CONDITIONAL STERILITY IN WHEAT

FIELD OF THE INVENTION

The invention relates to the production of hybrid seed in wheat by using a deacetylase gene to obtain conditional sterility. Vectors are described comprising a deacetylase gene under the control of promoters directing expression selectively in stamen cells in wheat, which are particularly suited for the production of wheat plants which can be made male-sterile upon application of N-acetyl-PPT.

All documents cited herein are included herein by reference.

BACKGROUND OF THE INVENTION

Deacetylases are capable of deacetylating acetylated toxins, such as N-acetyl-phosphinothricin (N-Ac-PTC or N-Ac-PPT), intracellularly, whereupon the cytotoxic activity of the toxins is restored (formation of PTC or PTC). U.S. Pat. No. 5,650,310, U.S. Pat. No. 5,668,297, U.S. Pat. No. 5,767,370, and U.S. Pat. No. 5,767,371, describe deacetylase genes, for the production of phosphinothricin or phosphinothricyl-alanyl-alanine, as well as processes for their isolation and use. Furthermore deacetylase genes are disclosed therein which are isolated from Streptomyces viridochromogenes (dea) and from *E. coli* (ArgE). The use of such genes for the production of plants with selectively destroyable plant parts is described therein. More specifically, a method is disclosed for the production of conditionally male-sterile plants. This is achieved by introducing a deacetylase gene, under the control of a tapetum-specific promoter into the genome of a plant. Upon application of N-Ac-PPT to the plant, in the tapetum cells, where the deacetylase is expressed, N-Ac-PPT is converted into PPT, which is toxic to the cells. The cytotoxic activity in the tapetum cells inhibits the development of microspores and renders the plant male-sterile.

WO 98/13504 describes the use of deacetylase genes for the production of female-sterile plants. WO 98/39462 describes a method of hybrid seed production using conditional female sterility, whereby a plant is made conditionally female-sterile by transformation with the ArgE gene linked to a female-preferential promoter.

WO 98/27201 describes novel genes encoding amino acid deacetylases isolated from Stenotrophomonas sp. (deac) and from Comamonas acidovorans (ama) and their use in the production of transgenic plants.

The high production cost of hybrid wheat has limited the use of commercial hybrids. The economic relationship between the additional costs of male sterilisation and seed production are up to now clearly unfavourable in breeding and agriculture. In contrast to crops such as maize, the hybrid seed production in wheat has been subject to considerable difficulties. The reproductive system of wheat, a self-fertilizer, is poorly adapted to cross-fertilization, which has led to poor hybrid seed set and consequently low yields. This has resulted in a high price for the hybrid seed on farm-level. In comparison to line varieties, the yield advantage of hybrids in wheat is up to now not sufficient enough to compensate high seed cost. (Picket, 1993, In: Hybrid Wheat-Results and Problems, Avances in Plant Breeding, Paul Parey Scientific Publishers, Berlin and Hamburg).

In the last few years, mainly due to an improvement in agricultural production steps, interest in hybrid wheat has resurfaced, and first hybrid wheat varieties have been marketed.

Traditional large-scale hybrid seed production is accomplished by planting separate rows or blocks of female parent lines and male parent lines as pollinators. Only the seed produced on the female parent rows or blocks is harvested. To ensure that this seed is hybrid seed, uncontaminated with selfed seed, pollination control must be implemented. Known pollination control methods are generally chemical, using a hybridising agent, or genetic. Genetic methods have been developed using either natural or molecular genes, based on either cytoplasmic or nuclear sterility factors. Neither the cytoplasmic male-sterility nor the chemical male-sterility are ideal and both show important economical, practical and/or enviromental drawbacks. The successful use of cytoplasmic male-sterility for commercial hybrid seed production requires a stable male cytoplasm and the availability of reliable restorer genes which is a limiting factor in the wheat system presently used based on the T. timopheevi system (Wilson, J. A. and Ross, W. M. (1962). Wheat Information Service, Kyoto University 14: 29–30; Wilson, J. A. and Ross, W. M. (1962b). Crop Science 2: 415–417). Furthermore such a system of cytoplasmic male sterility requires three lines to produce a single crossed hybrid: the A line (male-sterile), the B line (male-fertile maintainer), and an R line (male-fertile with restorer genes). Three-way crosses produced with cytoplasmic-genetic male sterility involve maintenance and production of four lines, the A and B lines of one inbred and male-fertile inbreds of the other two.

Alternatively, the production of hybrid seed can be achieved using chemicals that block or kill viable pollen formation. These chemicals, called gametocides, are used to impart a transitory male-sterility. The expense and the availability of the chemical, the reliability of the applications under different environments and the toxicity of the chemical to the environment however, limit its use in the production of hybrid seed.

Molecular methods for hybrid seed production offer a new promising alternative. Male-sterile wheat plants were obtained by introducing the barnase gene under the control of tapetum-specific promoters from corn and rice (De Block et al., 1997, Theor. Appl. Genet. 95:125–131). Such transformed plants are functionally male-sterile and can be used for the production of hybrid seed by crossing with male-fertile pollinator plants, containing corresponding restorer genes (to ensure restoration of fertility in the hybrid; as described in EP 344029, U.S. Pat. No. 5,689,041, U.S. Pat. No. 5,792,929, U.S. Pat. No. 5,723,763). The genetically engineered male sterility, whether it works through antisense or RNAse, can only be maintained in a heterozygous state. The heterozygous female parent, of which only 50% will be male sterile, must be planted in rows next to the pollen donor (male) parent and the other 50% of fertile female parent have to be removed. By genetic engineering it is possible to link the male sterility gene to a herbicide resistance gene and remove the fertile plants by spraying the corresponding herbicide. Still this system has economical drawbacks. Due to the fact that only 50% of the female plants can be used for hybrid seed production, the female parent rows must be planted at double density in order to obtain the same yield per acre. This will cause yield loss because of competition between plants. The herbicide spray also induces yield loss as resistant plants are never 100% resistant to the herbicide. The considerable costs for the chemical and for the "restorer" breeding program makes that this hybrid seed production system is economically not ideal for wheat. To achieve a more economical hybrid seed production system for wheat and potentially other cereal crops, the use of a conditional male-sterility system, whereby plants can be maintained in their male fertile form and no restorer genes are needed would be desirable. It remains to be described how such a conditional male-sterility system can optimally be developed for wheat and other cereal crops like barley, rye and oats.

SUMMARY OF THE INVENTION

The invention relates to a method for producing conditionally male-sterile wheat plants, which method comprises 1) introducing into the genome of a wheat cell or tissue a foreign DNA comprising a chimeric gene which comprises a DNA encoding a deacetylase, more specifically a deacetylase from Stenotrophomonas sp., under the control of a promoter directing expression selectively in stamen cells in wheat, and 2) regenerating a plant from the cell or tissue, which plant is conditionally male-sterile.

The invention further relates to a conditionally male-sterile wheat plant comprising, integrated into its genome, a foreign DNA comprising a chimeric gene which comprises:
  a) a DNA encoding a deacetylase, more specifically a deacetylase from Stenotrophomonas sp., under the control of
  b) a promoter directing expression selectively in stamen cells in wheat, such as the CA55 promoter, the T72 promoter or the E1 promoter;
whereby the wheat plant can be made male-sterile by application of an acetylated toxin, such as N-Acetyl-PPT, to the plant.

The invention further relates to a conditionally male-sterile wheat plant comprising, integrated into its genome, a foreign DNA comprising a chimeric gene which comprises a deacetylase coding sequence isolated from Stenotrophomonas sp., preferably from the organism deposited under accession No. DSM 9734 or a biologically active fragment or variant thereof; additionally or alternatively according to the present invention, the deacetylase coding sequence encodes the deacetylase corresponding to SEQ ID No. 8 described herein or a biologically active fragment or variant thereof; additionally or alternatively the DNA encoding a deacetylase of the invention comprises the sequence of SEQ ID No. 9, or a fragment or variant thereof and/or corresponds to a DNA sequence which hybridizes to SEQ ID No. 9 under standard stringent conditions.

The invention further relates to a method for producing composite hybrid seed in wheat, which comprises
  producing seeds capable of growing into conditionally male-sterile plants, comprising, integrated into their genome, a foreign DNA comprising a chimeric gene which comprises a DNA encoding a deacetylase from Stenotrophomonas sp. under control of a promoter directing expression selectively in stamen cells in wheat,
  interplanting these seeds with seeds capable of growing into male fertile plants,
  inducing male sterility in the conditionally male-sterile plants by applying an acetylated toxin, such as N-acetyl PPT to the conditionally male-sterile plants; and
  harvesting seed from both conditionally male-sterile plants and male fertile plants, which is composite hybrid seed.

The invention further relates to a method for producing pure hybrid seed in wheat by planting the above-described seeds capable of growing into conditionally male-sterile plants and seeds capable of growing into male-fertile plants in separate rows or blocks, and harvesting seed only from the pollinated conditionally male-sterile plants.

The invention further relates to a method for producing pure hybrid wheat seed by crossing conditionally male-sterile wheat plants, comprising integrated into their genome a DNA encoding a deacetylase from Stenotrophomonas sp. under control of a stamen selective promoter, with female sterile plants as described in U.S. Pat. No. 5,633,441 or U.S. Pat. No. 5,767,374 or conditionally female-sterile plants as described in WO 98/13504, which are male-fertile, and harvesting hybrid seed from the pollinated conditionally male-sterile plants.

The invention further relates to a conditionally male-sterile wheat plant comprising, integrated into its genome, a foreign DNA comprising chimeric gene which comprises a DNA encoding a deacetylase from Stenotrophomonas sp., under control of a stamen-selective promoter, and which further comprises a second chimeric gene which confers on the plant resistance to a herbicide.

The invention further relates to a conditionally male-sterile wheat plant, comprising the chimeric gene of the invention comprising a DNA encoding a deacetylase and further comprising a second chimeric gene which confers on the plant resistance to PPT. More specifically said second chimeric gene comprises a gene, such as the pat or bar gene, capable of converting PPT into N-acetyl-PPT. The N-acetyl-PPT so produced can be transported through the plant to the stamen cells in which the deacetylase is expressed, where it can be converted to PPT. It is understood that in this embodiment of the invention, specific destruction of the stamen cells can be induced by treatment of the plant with N-acetyl PPT or PPT.

The invention further relates to a method for producing pure hybrid seed in wheat, which comprises:
  producing seeds capable of growing into conditionally male-sterile plants comprising, integrated in their genome, a foreign DNA comprising
    a) a chimeric gene comprising a DNA encoding a deacetylase from Stenotrophomonas sp. under control of a promoter that directs stamen selective expression in wheat, and further comprising
    b) a chimeric gene which confers on the plants resistance to a herbicide,
  interplanting seeds capable of growing into conditionally male-sterile plants with seeds capable of growing into male fertile plants, that are not resistant to the herbicide,
  inducing male-sterility in the conditionally male-sterile plants by applying an acetylated toxin, such as N-acetyl PPT, to the conditionally male-sterile plants;
  allowing pollination of the male-sterile plants by the male fertile plants;
  applying the herbicide to eliminate the male fertile plants; and
  harvesting seed from the conditionally male-sterile plants.

The present invention also demonstrates that particular stamen selective promoters, particularly the CA55 promoter, the PE1 promoter, and the T72 promoter are particularly useful, when linked to a deacetylase gene, for the generation of conditionally male-sterile plants according to the invention.

The present invention further demonstrates that the deac system is particularly suited for obtaining inducible male sterility in cereal plants, such as barley, oats, rye and most particularly in wheat.

DETAILED DESCRIPTION OF THE INVENTION

Figure 1:
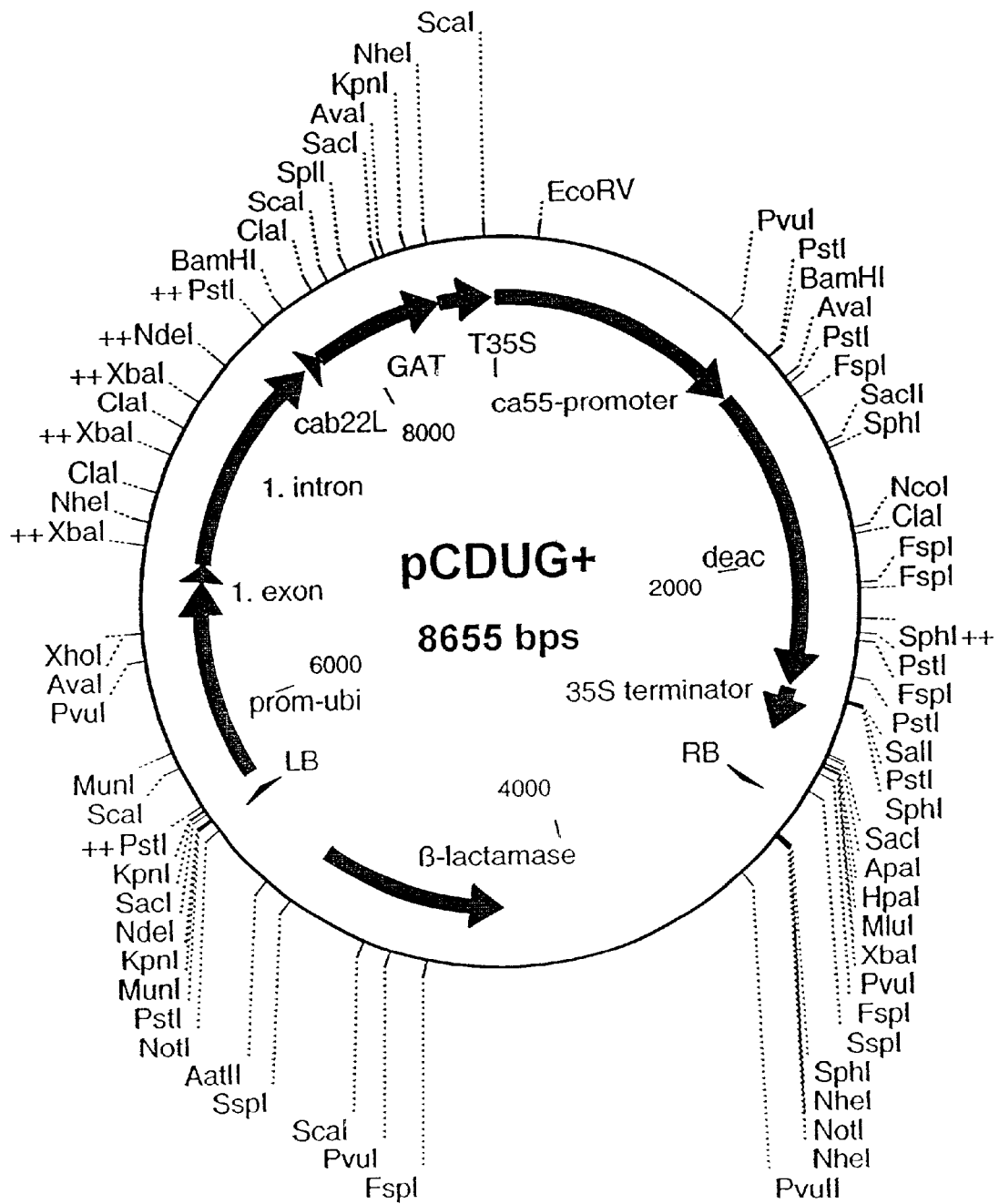
FIG. 1: Plasmid map of pCDUG+, comprising the elements as described in Table 1.
Figure 2:
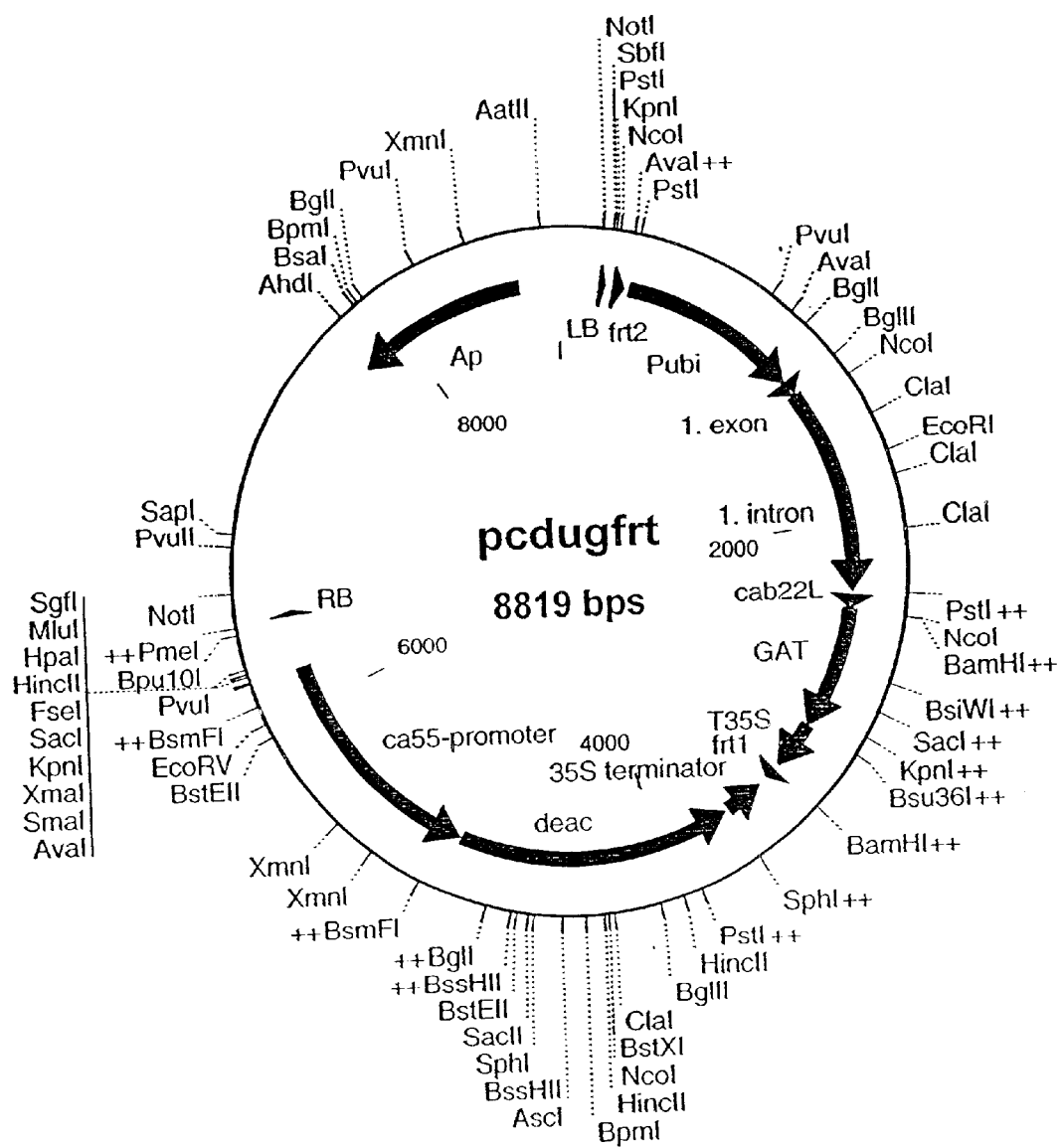
FIG. 2: Plasmid map of pCDUGFRT, comprising the elements as described in Table 1, as well as the target sequences for the frt/flp excision system at the 5' and 3' end of the marker gene.
Figure 3:
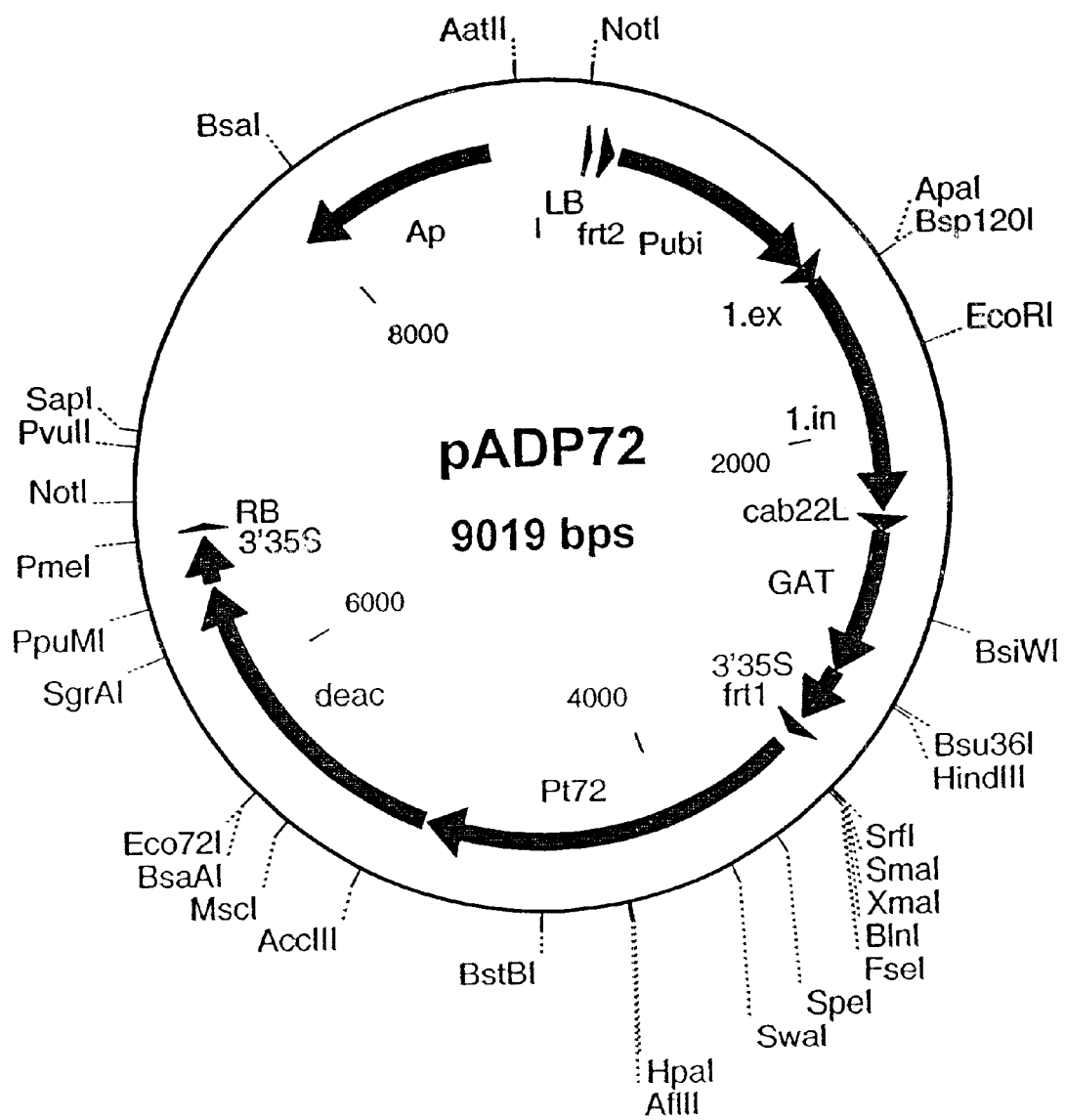
FIG. 3: Plasmid map of pADP72, comprising the deac gene of Stenotrophomonas sp. under control of a T72 promoter

The invention relates to a conditionally male-sterile wheat plant, comprising a deacetylase coding sequence placed under the control of a promoter directing stamen-selective expression in wheat. The deacetylase of the invention, more specifically the deacetylase encoded by the deac gene from Stenotrophomonas sp., is capable of deacetylating an acetylated toxin in wheat cells, rendering it toxic to the wheat plant cell in which it is expressed. As described herein, the acetylated toxin, more specifically N-acetyl-PPT, when applied to a wheat plant, is transported to the stamen cells, where in the presence of a deacetylase, it is converted to a toxin, more specifically PPT, which is toxic to the cells.

The term "gene" as used herein refers to any DNA sequence comprising several operably linked DNA fragments such as a promoter and a 5' regulatory region (which together form the promoter region), a coding sequence, and an untranslated 3' region comprising a polyadenylation site.

The term "chimeric" when referring to a gene or DNA sequence is used to refer to the fact that in nature, the coding sequence is not associated with the promoter or with at least one other regulatory region of the DNA in the gene.

A "chimeric gene" as used herein may comprise one or more genes or DNA sequences as described above. "Foreign" when referring to a gene or a DNA sequence with respect to a plant species is used to indicate that the gene or DNA sequence is not naturally found in that plant species or is naturally located in a different locus in the genome of that plant species.

A genome of a plant, plant tissue or plant cell, as used herein, refers to any and all genetic material in the plant, plant tissue or plant cell, and includes both the nuclear and the plastid (chloroplast) and mitochondrial genome.

A DNA molecule or coding sequence encoding a deacetylase as used herein refers to a DNA sequence encoding a protein having the activity of a deacetylase. A deacetylase is a molecule which is capable of deacetylating an acetylated toxin (which in itself—i.e. in the absence of a deacetylase—is not toxic to the plant or its plant cells) to produce the active toxin. Preferably, the deacetylase is capable of deacetylating N-acetyl PPT, to produce PPT which is cytotoxic. Deacetylase activity can be measured by radioactive or non-radioactive assays as described in WO 98/27201 and U.S. Pat. No. 5,668,297.

According to the present invention, a preferred embodiment of the DNA encoding a deacetylase, also referred to herein as a "deac" coding sequence, is a DNA encoding a deacetylase from Stenotrophomonas sp., or a biologically active fragment or variant thereof. A "fragment" of a sequence means a truncated sequence of the original sequence (nucleic acid or amino acid) referred to, which is sufficient to ensure the (encoded) protein to be biologically active.

A variant of a sequence (nucleic acid or amino acid) refers to a sequence which is essentially similar, meaning that when two sequences are aligned, the percent sequence identity, i.e. the number of positions with identical nucleotides or amino acids divided by the number of nucleotides or amino acids in the shorter of the sequences, is higher than 80%, preferably higher than 90%. The alignment of two nucleotide sequences is performed by the algorithm as described by Wilbur and Lipmann (1983, Proc. Natl. Acad. Sci. U.S.A. 80:726) using a window size of 20 nucleotides, a word length of 4 nucleotides, and a gap penalty of 4. Preferably a variant of a DNA encoding a deacetylase as used herein is a variant of a deacetylase gene from Stenotrophomonas sp., which has been adapted for preferred codon usage in monocots, particularly wheat.

In a preferred embodiment of the invention, the DNA encoding a deacetylase used in the context of the present invention, is a DNA which can be isolated from the deposit with deposit No. DSM 9734 (as described in WO 98/27201). More specifically such a DNA is a DNA encoding a deacetylase having the sequence of SEQ ID No 8, or a biologically active fragment thereof. Additionally or alternatively such a DNA can comprise the DNA sequence of SEQ ID No. 9, or a variant or fragment thereof, or can correspond to a DNA sequence which hybridizes with the sequence of SEQ ID No. 9 under standard stringent conditions. Standard stringent conditions as used herein refers to the conventional hybridizing conditions as described by Sambrook et al. (1989) Molecular Cloning: A Laboratory Manual, Second Edition, Cold Spring Harbor Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1%SDS, 6) washing the filter three times for 20 min. each at 68° C. in 0.2×SSC, 0.1%SDS, and 7) exposing the filter for 24 to 48 hours to X-ray film at −70° C. with an intensifying screen.

Other nucleotide sequences encoding deacetylases that can be used in the context of the present invention have been isolated, such as the dea gene from Streptomyces viridochromogenes and the ArgE gene from *E. coli* (U.S. Pat. No. 5,767,371), and the Ama gene from Comamonas acidovorans (WO 98/27201).

As used herein "N-acetyl-PPT" refers to N-acetyl-phosphinothricin, or a composite structure thereof, such as, but not limited to N-acetyl-phosphinothricyl-alanyl-alanine (PTT), which in itself is not toxic to cells but is converted to a toxin by a deacetylase. Thus, the term N-acetyl-PPT refers to any formulation of N-acetyl-phosphinothricin, or derivatives or related compounds, such as acetylated forms of desmethylphosphinothricine (2-amino-4-hydroxyphosphinobutyric acid), acetylated forms of bialaphos (phosphinothricyi-alanyi-alanine), acetylated forms of desmethylbialaphos and the like, their salts, racemic mixtures and active enantiomers, which can be used in the context of the present invention.

According to the present invention, a "stamen-selective promoter" or a promoter that directs expression selectively in stamen cells is a promoter directing expression in selective stamen cells (including anther cells and pollen) in wheat, preferably directing expression essentially only in stamen cells in wheat. More specifically, the stamen-selective promoter is a tapetum-specific promoter directing expression specifically in tapetum cells in wheat. More specifically, the stamen-selective promoter as used herein refers to a promoter selected from the CA55 promoter isolated form corn (WO 92/00275, U.S. Pat. No. 5,589,610), the T72 or the E1 promoter isolated from rice (U.S. Pat. No. 5639948), which were shown to cause male-sterility when linked to a bamase coding sequence in wheat (De Block et al, supra). Other stamen specific promoters which have been isolated and can be used in the context of the present invention are, for example but not limited to, the stamen-specific promoters TA29 (U.S. Pat. No. 5,652,354), SGBG (U.S. Pat. No. 5,837,850), and 5126 (U.S. Pat. No. 5,689,049).

Additionally, it can be envisaged that promoters of genes involved in the early development of the stamen can be used in the context of the present invention.

A "male-sterile plant" as used herein refers to a plant that is not capable of producing viable, fertile pollen. In the context of the present invention, a male-sterile plant as used herein is female fertile (and can thus function as a female parent to produce seed when pollinated by a male-fertile plant). A "conditionally male-sterile plant" refers to a plant which, under normal growing conditions, is male fertile, i.e. produces viable, fertile pollen, and which can be made male-sterile under specific conditions. More specifically, these conditions are understood to refer to the treatment of the plant with an acetylated toxin, which normally is not toxic to the plant or plant cells, but in the presence of a deacetylase in the plant cell is converted into a substance which is cytotoxic.

"Treatment" of the plant can refer to administering the substance in any way, such as, but not limited to manual treatment, or spraying of the plant, plant part (or of the field or greenhouse wherein the plant is grown), or through other forms of irrigation, which can lead to uptake of the substance by leaves, roots, or other tissues.

It is described herein that treatment of the leaf cells of a wheat plant with N-acetyl PPT will result in uptake of N-acetyl PPT by the leaf cells and transportation to different plant organs. Thus, treatment of a wheat plant which comprises a chimeric gene comprising a deacetylase coding sequence expressed in specific cells of the plant, will result in the conversion of N-acetyl PPT to PPT in those cells, causing these cells to die.

In a specific embodiment of the invention, the transgenic plant, comprising in its genome the DNA molecule of the invention encoding a protein having the biological activity of a deacetylase, additionally comprises a chimeric gene conferring on said plants resistance to PPT, such as, but not limited to the herbicide resistance genes, pat or bar described in EP-A-0 242 236, EP-A-0 242 246, EP-A-0 257 542, EP-A-0 531 716. These genes encode enzymes which are capable of converting PPT into N-acetyl-PPT. This N-acetyl-PPT can be transported throughout the plant and act as the substrate for a deacetylase specifically expressed in certain plant cells or tissues. It is understood that according to this specific embodiment, induction of tissue-specific cytotoxicity will also occur upon treatment of the plant with PPT.

A "female-sterile plant" as used herein refers to a plant that cannot produce viable seed. In the context of the present invention a female-sterile plant is male fertile, i.e. capable of producing viable pollen (and can thus finction as the male-parent or pollinator). Female sterility can be the result of breeding selection or due to the presence of a transgene (such as, but not limited to those described in U.S. Pat. No. 5,633,441, U.S. Pat. No. 5,767,374). A conditionally female sterile plant refers to a plant which under normal growing conditions is female fertile and which can be made female sterile under specific conditions. Examples of conditionally female sterile plants that are made sterile by application of an N-acetyl-PPT, are described in WO 98/13504.

"Interplanting" as used herein refers to a method of planting seeds or plants in the field that ensures adequate cross-pollination of the conditionally male-sterile plants by the male-fertile plants. This can be achieved by either random mixing of female and male parent seed in different blends (80/20; 90/10; etc.) before planting or by planting in specific field patterns, whereby different seeds are alternated. When separate harvesting from different plants is required, planting in alternating blocks or rows are preferred.

A "chimeric marker gene" as used herein is a gene comprising a marker DNA under the control of a promoter that is active in plant cells. The marker DNA encodes an RNA, protein or polypeptide, which, when expressed in a plant or plant cell, allows such plants or plant cells to be distinguished and separated from plants or plant cells not expressing the marker DNA. Examples of marker genes are genes that provide a specific color to the cells (such as the Al gene, Meyer et al. 1987, Nature 330:667) or genes that encode a particular resistance to the plant cells or the plant such as antibiotic resistance (e.g. the aac(6') gene, encoding resistance to gentamycin, WO94/01560).

Preferred marker genes are herbicide resistance genes. A herbicide resistance gene as used herein is a gene conferring to the plant or plant cell resistance to a herbicide. In the context of the present invention, the herbicide resistance gene can also be used to eliminate wheat plants that do not comprise the herbicide resistance gene in their genome. Particularly it can be used in the production of hybrid wheat seed for the elimination of male-fertile wheat plants (that are female fertile) after pollination of the male-sterile plants has occurred, to avoid production of selfed seed on the male-fertile plants, which contaminate the hybrid seed during harvest. Examples of herbicide resistance genes are the genes encoding resistance to phenmedipham (such as the pmph gene, U.S. Pat. No. 5,347,047; U.S. Pat. No. 5,543,306), the genes encoding resistance to glyphosate (such as the EPSPS genes, U.S. Pat. No. 5,510,471), genes encoding bromoxynil resistance (such as described in U.S. Pat. No. 4,810,648) genes encoding resistance to sulfonylurea (such as described in EPA 0 360 750), genes encoding resistance to the herbicide dalapon (such as described in WO 99/27116), and genes encoding resistance to cyanamide (such as described in WO 98/48023 and WO 98/56238) and genes encoding resistance to glutamine synthetase inhibitors, such as PPT (such as described in EP-A-0 242 236, EP-A-0 242 246, EP-A-0 257 542).

Preferably, the herbicide resistance gene is a gene which also confers resistance to a herbicide which is particularly useful for wheat production, i.e. a herbicide which is capable of controlling the major weeds of wheat, such as annual grassy weeds including wild oats, green and yellow foxtail (wild millet), broadleaf weeds including annual sunflower, burdock, chickweed, cocklebur, corn spurry, cow cockle, field horsetail, flixweed, green smartweed, hemp-nettle, hoary cress, kochia, lady's-thumb, lamb's-quarters, mustards (except dog and green tansy), plantain, prickly lettuce, ragweeds, redroot pigweed, Russian pigweed, Russian thistle, shepherd's-purse, stinkweed, vetch, volunteer canola (rapeseed), wild buckwheat, and wild radish.

For specific applications of the present invention it can be desirable to remove the marker gene from the plant (i.e. to avoid stacking of marker genes). This can be achieved by site-specific homologous recombination also referred to as the "Kick/Out-system". The marker gene to be kicked out is flanked by excision sites in the transformation construct, which are specifically recognized by a recombinase. Crossing of a plant carrying the marker gene flanked by specific excision sites with a plant carrying a gene encoding the corresponding recombinase, results in excision of the marker gene in the progeny. Examples of such site-specific homologous recombination systems are the flp/frt system (Lyznik et al., 1993, Nucleic Acids Res. 21:969–975; Lyznik et al., Nucleic Acids Res. 1996, 24:3784–3789), and the Cre/Lox system (Bayley, C. C. et al., 1992, Plant Mol. Biol. 18, 353–361).

The cytotoxic effect of certain toxins may be enhanced by targeting to the specific parts of the cell, such as the chloroplast or mitochondria. Phosphinothricin is a glutamine synthase inhibitor. In plants, glutamine synthase exists in multiple isozymic forms that can be localized within the cell in the cytosol and plastids. Thus, it is contemplated that targeting of the deacetylase to the chloroplast, whereby N-acetyl-PPT is converted to PPT in the chloroplast, increases cytotoxic efficiency. Thereto, the foreign DNA comprising the deacetylase coding sequence can comprise an additional foreign DNA encoding a transit peptide. The additional DNA is preferably located between the promoter and the deacetylase coding sequence. Alternatively, it can be desired that the marker protein or polypeptide is transported from the cytoplasm into chloroplasts or mitochondria of the transformed plant cells. Thereto, an additional DNA encoding a transit peptide is located between the marker DNA and its promoter. By transit peptide is meant a polypeptide fragment which is normally aassociated with a chloroplast or mitochondrial protein or subunit of the protein and is produced in a cell as a precursor protein encoded by the DNA of the cell. The transit peptide is responsible for the translocation process of the nuclear-encoded chloroplast or mitochondrial protein or subunit into the chloroplasts or mitochondria, and during such a process, the transit peptide is separated or proteolytically removed from the chloroplast or mitochondrial protein or subunit. One or more of such additional DNA's can be provided in the foreign DNAs of this invention as generally described and exemplified in European patent publication (EP) 0 189 707 and EP 0 344 029. Alternatively, the transit peptide can be an artificially engineered sequence which has been designed and/or selected to be able to function as such.

Transformation of the plants of the invention can occur in a number of ways described in the art. Such methods include, but are not limited to Agrobacterium-mediated transformation (EP 0 116 718, DeBlaere et al., 1987, Meth. Enzymol. 153:277–293), or direct gene transfer (U3S 5,712, 135; Pazkowski et al., 1984, EMBO J. 3:2717–2722; Crossway et al., 1986, Mol. Gen. Genet. 102:179; Riggs et al., 1986, Proc. Natl. Acad. Sci. USA 83:5602–5606; WO92/09696; Potrykus et al. 1991, Annu. Rev. Plant Physiol. Plant Mol. Biol. 42:205–225); see also Christou P. 1994, Agro-Food Industry Hi-Tech 2:17; Langridge et al. 1992, Plant J. 2:631; Vasil , 1994, Plant Mol. Biol. 25:925; Chen D., 1998, Methods Mol. Biol. 81:373.

Alternatively, the foreign DNA comprising the DNA encoding a deacetylase of the invention can be inserted into the plastid genome of the cell or cells of a plant. Gene transfer can be carried out, for example, by particle gun bombardment (as described by Svab et al., 1990, Proc. Natl. Acad. Sci. USA 87:8526–8530) or by Agrobacterium-mediated transformation (De Block et al., 1985, EMBO J. 4:1367). It is understood that in this case, suitable promoters, i.e. that are active in plastids, need to be used.

The present invention relates particularly to cereal crops, such as barley, rye, oats and most particularly wheat. Most cultivated wheat plants belong to the *Triticum aestivum* species, but other cultivated or wild forms may also be used.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is fulnctionally or structurally defined, may comprise additional DNA sequences, etc.

Unless otherwise stated, all recombinant DNA techniques are carried out according to standard protocols as described in Sambrook et al. (1989) Molecular Cloning: A Laboratory Manual, Second Edition, Cold Spring Harbour Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

Sequence Listing.

SEQ ID No. 1: sequence of the Not I fragment of pCDDUG+

SEQ ID No. 2: primer GAT1

SEQ ID No. 3: primer GAT2

SEQ ID No. 4: primer CA6

SEQ ID No. 5: primer 7PA

SEQ ID No. 6: primer CA1

SEQ ID No. 7: primer CA2

SEQ ID No. 8: amino acid sequence of a deacetylase from Stenotrophomonas sp.

SEQ ID No. 9: DNA sequence encoding a deacetylase from Stenotrophomonas sp.

EXAMPLES

Example 1

Foliar Uptake and Distribution of 14C-labeled N-Acetyl-PPT in Wheat

*Triticum aestivum* plants were cultivated in outdoor conditions and treated in stage 32 (BBCH scale, =2nd node detectable, ear length about 2.5 cm) with the test compound dinatrium L-2-acetamido-4-methylphosphinato-butyrate-[$3^{14C}$, $4^{14C}$] (spec. activity 6777 MBq/g).

The concentration of the test compound was 0.1% active ingredient in application solution, which corresponded to the aqueous solution of Basta®.

Plant treatment: The application solution of the formulated test compound was applied in the form of microdroplets by syringe to the blades (adaxial surface) of the fuilly developed leaves. A volume of 20 µl each was applied to the 3rd or 4th leaf of the main shoot and of two tillers per plant (=a total of 60 µl application solution per plant.). Plants were kept under outdoor conditions and uptake and translocation of the test substance was analyzed at different stages.

Sampling of Leaf Tissue was Carried Out at the Following Time Points:
1) 1 week after treatment
2) 3 weeks after treatment
3) heading stage
4) grain maturity Processing of Collected Samples for quantitative Determinations:

For the sampling done at time points 1, 2 and 3, the treated leaf blades were cut off and the non-absorbed test compound was washed from the treated leaf blades by 2 consecutive short washes with water. Subsequently plants were dissected further, resulting in the following parts:

treated leaf blades ear (sampling time point 3 only)

rest of shoot root

Radioactivity was quantified in the different plant parts and in the washing solutions and was calculated as equivalents of the labeled compounds. The chemical nature of the radioactive residue is identified in the ears.

For the sampling time point 4, radioactivity is determined in the grains only and is calculated as equivalents of the labeled test compound. The chemical nature of the radioactive residue is identified if the residue level permits.

In addition to the quantitative radioactivity measurements the distribution of radioactivity is determined by autoradiography in plants of the sampling time points 1 and 2.

Based on measurements of radioactivity in the samples taken at different time points as well as on the autoradiography of plant material taken at time points 1 and 2, it can be concluded that there is good foliar uptake of N-acetyl PPT in wheat tissue and there is translocation through the phloem to the ears both in the main shoot and the tillers.

Example 2

Construction of Vectors for the expression of the Deacetylase Gene in Wheat a) Vectors Comprising the Deac Coding Sequence Under Control of the CA55 Promoter The vector pCDUG+ (FIG. 1) was made by introducing the following structural elements into pUC18:

- a marker gene cassette comprising the Ubiquitin promoter from maize containing its first exon and first intron, linked to the 5' untranslated leader sequence of the cab22L gene from pea, operably linked to the gentamycin acetyltransferase (GAT) coding sequence and the 3' untranslated region from the CaMV 35S transcript.
- a deac gene expression cassette comprising the tapetum-specific promoter CA55 from maize (WO 92/13956) operably linked to the deac coding sequence (WO 98/27201) and the 3' untranslated region from the CaMV 35S transcript.

The complete insert is flanked by left and right T-DNA border sequences from Ti-plasmid pTIT37 of Agrobacterium tumefaciens (Caplan et al., 1983, Science 222:815–8520; Depicker et al. 1982, J. Mol. Appl. Genet. 1:561–573).

The coordinates of the described genetic elements are given in Table 1. The complete insert comprising marker and deac cassette is isolated as a 6367 bp Notl fragment by HPLC and used for plant transformation. The DNA sequence of this fragment is provided in SEQ ID NO. 1.

TABLE 1

T-DNA of pCDUG+

| Position | Description |
|---|---|
| 9–36 | Left T-DNA border from pTIT37 |
| 116–1020 | Ubiquitin promoter from maize |
| 1021–1101 | 1st exon of ubi gene |
| 1102–2111 | 1st intron of ubi gene |
| 2133–2199 | 5' untranslated leader sequence from cab22 gene from pea |
| 2201–2812 | Gentamycin acetyltransferase coding sequence |
| 2815–3049 | 3' untranslated region from CaMV 35S transcript |
| 3071–4248 | CA55 promoter from maize |
| 4261–5625 | Deac coding sequence from *Stenotrophomonas sp.* |
| 5646–5841 | 3' untranslated region from CaMV 35S transcript |
| 6094–6118 | Right T-DNA border from pTIT37 |

Alternative constructs are made to allow for the possibility of removing the marker gene cassette. In these alternative constructs, the whole marker gene cassette is flanked by frt1/frt2 sequences (described by Lyznik et al., 1993, 1996, above) as part of the frt/flp excision system. A schematic representation of this plasmid (PCDUGFRT) is provided in FIG. 2.

b) Vectors Comprising the Deac Coding Sequence Under Control of the T72 or E1 Promoters The vector pADP72 (FIG. 3) was made by introducing the following structural elements into pUC 18:

- a marker gene cassette comprising the Ubiquitin promoter from maize containing its first exon and first intron, linked to the 5' untranslated leader sequence of the cab22L gene from pea, operably linked to the gentamycin acetyltransferase (GAT) coding sequence and the 3' untranslated region from the CaMV 35S transcript. The whole marker gene cassette is flanked by frt1/frt2 sequences (described above) as part of the flp/frt excision system.
- a deac gene expression cassette comprising the tapetum-specific promoter T72 from rice (U.S. Pat. No. 5,639,948) operably linked to the deac coding sequence and the 3' untranslated region from the CaMV 35S transcript (as described above).

The complete insert is flanked by left and right T-DNA border sequences from Ti-plasmid pTIT37 of Agrobacterium tumefaciens (as described above).

The coordinates of the described genetic elements are given in Table 2. The complete insert comprising marker and deac cassette is isolated as a 6577 bp Not I fragment and used for plant transformation.

TABLE 2

T-DNA of pADP72

| Position | Description |
| --- | --- |
| 12–35 | Left T-DNA border from pTIT37 |
| 77–130 | Target sequence for frt/flp excision system |
| 157–1061 | Ubiquitin promoter from maize |
| 1062–1142 | 1st exon of ubi gene |
| 1143–2152 | 1st intron of ubi gene |
| 2174–2240 | 5' untranslated leader sequence from cab22 gene from pea |
| 2242–2853 | Gentamycin acetyltransferase coding sequence |
| 2856–3090 | 3' untranslated region from CaMV 35S transcript |
| 3123–3176 | Target sequence for frt/flp excision system |
| 3238–4835 | PT72 promoter from rice |
| 4850–6214 | Deac coding sequence from *Stenotrophomonas sp.* |
| 6235–6430 | 3' untranslated region from CaMV 35S transcript |
| 6458–6481 | Right T-DNA border from pTIT37 |

Figure 4:
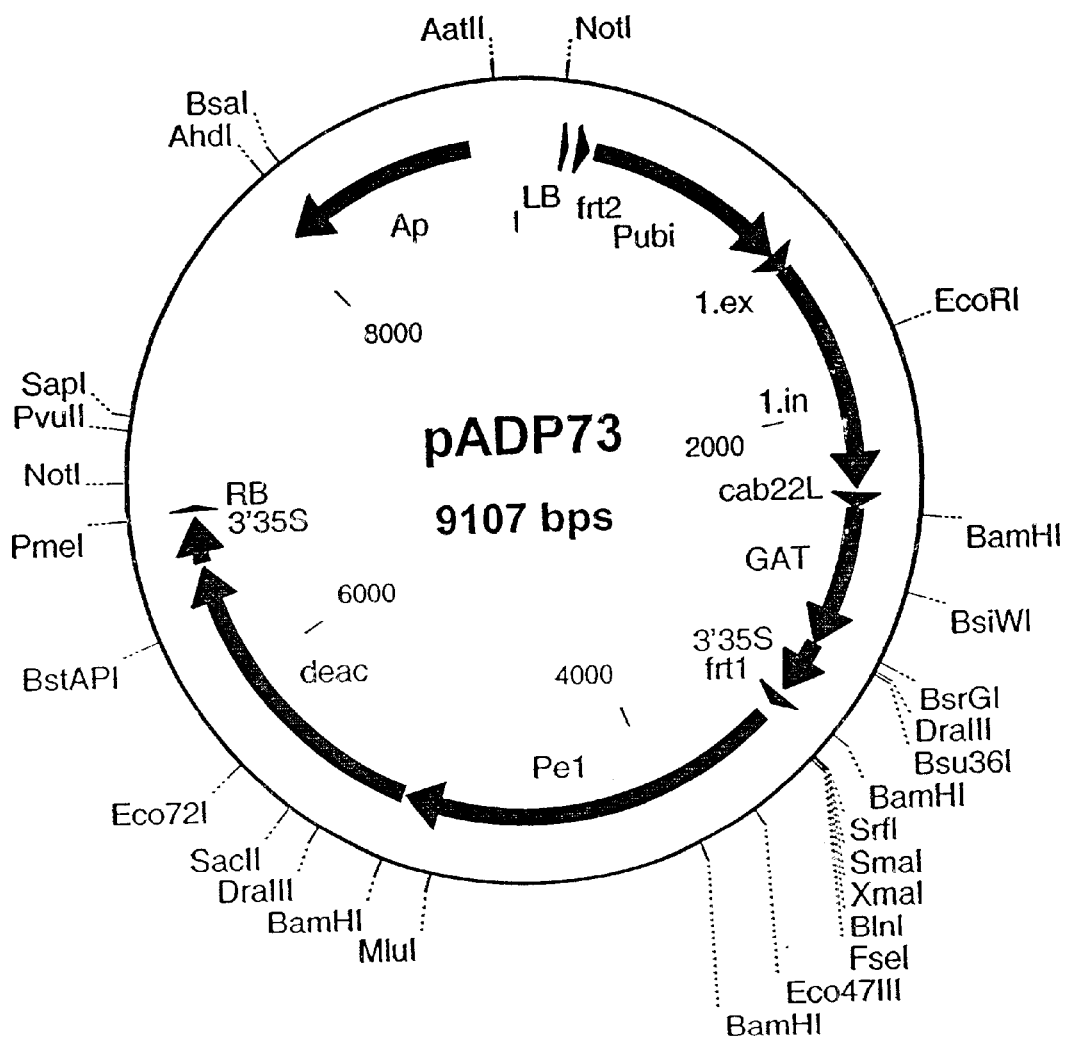
FIG. 4: Plasmid map of pADP73, comprising the deac gene of Stenotrophomonas sp. under control of an E1 promoter

The vector pADP73 (FIG. 4) was made by introducing the following structural elements into pUC18:

a marker gene cassette comprising the Ubiquitin promoter from maize containing its first exon and first intron, linked to the 5' untranslated leader sequence of the cab22L gene from pea, operably linked to the gentarnycin acetyltransferase (GAT) coding sequence and the 3' untranslated region from the CaMV 35S transcript. The whole marker gene cassette is flanked by frt1/frt2 sequences (described above) as part of the flp/frt excision system.

a deac gene expression cassette comprising the tapetum-specific promoter E1 from rice (U.S. Pat. No. 5,639,948) operably linked to the deac coding sequence and the 3' untranslated region from the CaMV 35S transcript as described above.

The coordinates of the described genetic elements are given in Table 3. The complete insert comprising marker and deac cassette is isolated as a 6665 bp Not I fragment by HPLC and used for plant transformation.

TABLE 3

T-DNA of pADP73

| Position | Description |
| --- | --- |
| 12–35 | Left T-DNA border from pTIT37 |
| 77–130 | Target sequence for frt/flp excision system |
| 157–1061 | Ubiquitin promoter from maize |
| 1062–1142 | 1st exon of ubi gene |
| 1143–2152 | 1st intron of ubi gene |
| 2174–2240 | 5' untranslated leader sequence from cab22 gene from pea |
| 2242–2853 | Gentamycin acetyltransferase coding sequence |
| 2856–3090 | 3' untranslated region from CaMV 35S transcript |
| 3123–3176 | Target sequence for frt/flp excision system |
| 3237–4923 | PE1 promoter from rice |
| 4938–6302 | Deac coding sequence from *Stenotrophomonas sp.* |
| 6323–6518 | 3' untranslated region from CaMV 35S transcript |
| 6546–6569 | Right T-DNA border from pTIT37 |

Example 3

Transformation of *Triticum aestivum* (Wheat)

A number of different cultivars of spring (sw) and winter wheat (ww) were used to establish optimal transformation and regeneration conditions.

Seeds were grown in soil and cultured in growth chambers or in the greenhouse until flowering. The maturity status of the kernels was checked regularly to determine which spikes could be collected for transformation purposes.

After collection of the spikes, the immature kernels were isolated by separating them from the glumes surrounding them. The kernels were then surface-sterilized for 1 min. in 70% ethanol and for 15 min. in a sodium hypochlorite solution with about 1.3% active chlorine. Finally, the immature kernels were rinsed 3 times in sterile water.

Wheat tissue was transformed with the plasmid DNA using direct gene transfer and regenerated to plants on appropriate media.

The small plantlets initiated on the selective regeneration media were transferred to hormone-free medium for elongation. Well elongated plantlets were then transferred to the growth chambers or to the greenhouses.

Example 4

Selection of Transformants

Primary transformants (T0) were tested for correct transformation by PCR and southern blot analysis (described below).

T0 plants are screened for deacetylase activity in the anthers as described below to identify positive transformation events. T0 plants are then selfed for the production of T1 progeny. These plants are sprayed with acetyl PPT (1–3 sprays of 5 mg/ml of N-acetyl PPT 2–3 weeks before inflorescence formation) and flowers are evaluated for male sterility.

Homozygous T1 and subsequent homozygous generations are sorted out and are analyzed by PCR and Southern blot (described below) to determine the copy number of the transgene.

Deacetylase Assay with [$^{14}$C]-N-acetyl-PPT

Deacetylase activity in the anthers of transgenic plants is tested using the following protocol:

Anthers are harvested from 2 flowers and homogenized in an Eppendorf tube in 50 µl uptake buffer (10 mM NaCl, 10 mM NaPhosphate, pH=7.5).

Cell debris is then pelleted in a microcentifuge and the supernatant is dialyzed for 2 h against uptake buffer.

The dialyzed crude extract (10 µl) is incubated with 1 µL [$^{14}$C]-N-acetyl-PPT (at a 1:40 dilution from the stock solution of 1 mM) overnight at 37° C.

The assay solution is loaded (5 µl) onto TLC-plates (Merck, HPTLC-cellulose, ref. 15035), which are developed in a 3:2 solution of 2×n-propanol:25% ammonia. Control samples loaded are [$^{14}$C]-N-acetyl-PPT and [$^{14}$C]-PPT.

Kodak XAR5 film is exposed to the TLC plates for 2–3 days.

Remaining crude extracts can be stored in the freezer and used for determination of protein content.

Southern Blotting

Presence of the transgene is checked by standard Southern blot analysis using the DNeasy Plant Mini Kit (Quiagen, Catalog Nr. 69103). 10 µg of DNA are digested with BamHI, EcoRI, HindIII, and SalI, respectively.

Southern blots are prepared using standard protocols as described by Maniatis et al. (above). For the pCDUG transformants, a 1.4-kb BamHI/SalI fragment from plasmid pCDUG, carrying the deac structural gene, is isolated and labeled with alpha-[32P]-dCTP by random primer labelling using the Megaprime kit from Amersham. Similar fragments are isolated from the pCDUGFRT, pADP72 and pADP73 vectors.

The fragments are used as probes for Southern hybridization in 50% formamide at 42° C. Conditions for hybridization, filter washing and X-ray film exposure are as described by Maniatis et al., 1989.

PCR

Presence of the transgene was checked with a PCR using specific primers for the GAT gene and specific primers for the deac coding sequence and the CA55, T72 and E1 promoters.

Genomic DNA was isolated from plant tissue according to the protocol described for the DNeasy Plant Mini Kit (Qiagen, Catalog Nr. 69103).

The primers used for identification of the plants transformed with pCDUG+ or pCDUGFRT were as follows:

a) GAT specific primers:

|  | sequence (5' → 3') | position in pCDUG+ |
|---|---|---|
| GAT1: | GCACCGATTCCGTCACACTGC | 2268 → 2286 |
|  | (SEQ ID No 2) |  |
| GAT2: | GTACACGGCTGGACCATCTGG | 2744 ← 2764 |
|  | (SEQ ID No 3) |  | b) deac-specific primers

|  | sequence (5' → 3') | position in pCDUG+ |
|---|---|---|
| CA6: | GTTACGAGCACGTAGTTGGCG | 4054 → 4074 |
|  | (SEQ ID No 4) |  |
| 7PA: | GCTCATGGGAGGTCCTTCTTC | 5607 ← 5627 |
|  | (SEQ ID No 5) |  | c) CA55-specific primers:

|  | sequence (5' → 3') | position in pCDUG+ |
|---|---|---|
| CA1: | TACGCCCCGGGTGGTATGCATCAATAGAGCCG | 3071 → 3092 |
|  | (SEQ ID No 6) |  |
| CA2: | TACGCGGATCCGCTGCAGCTAGTTAGCTCGAT | 4227 ← 4248 |
|  | (SEQ ID No 7) |  |

Standard PCR's were carried out in 50 μl assays containing 10 ng of genomic plant DNA as template and 0.2 μM of each primer.

In reactions containing deac-specific primers 6.7% glycerol and 5% DMSO was included in the assay.

| Cycling parameters: | denaturation | 5 min. at 94° C. |
|---|---|---|
|  | 25 cycles: | 1 min. at 94° C. |
|  |  | 1 min. at 60° C. |
|  |  | 2 min. at 72° C. |
|  | final extension: | 10 min. at 72° C. |

10 μl of the reactions were analyzed on 1% agarose gels in order to identify the correct amplification products.

Figure 5:
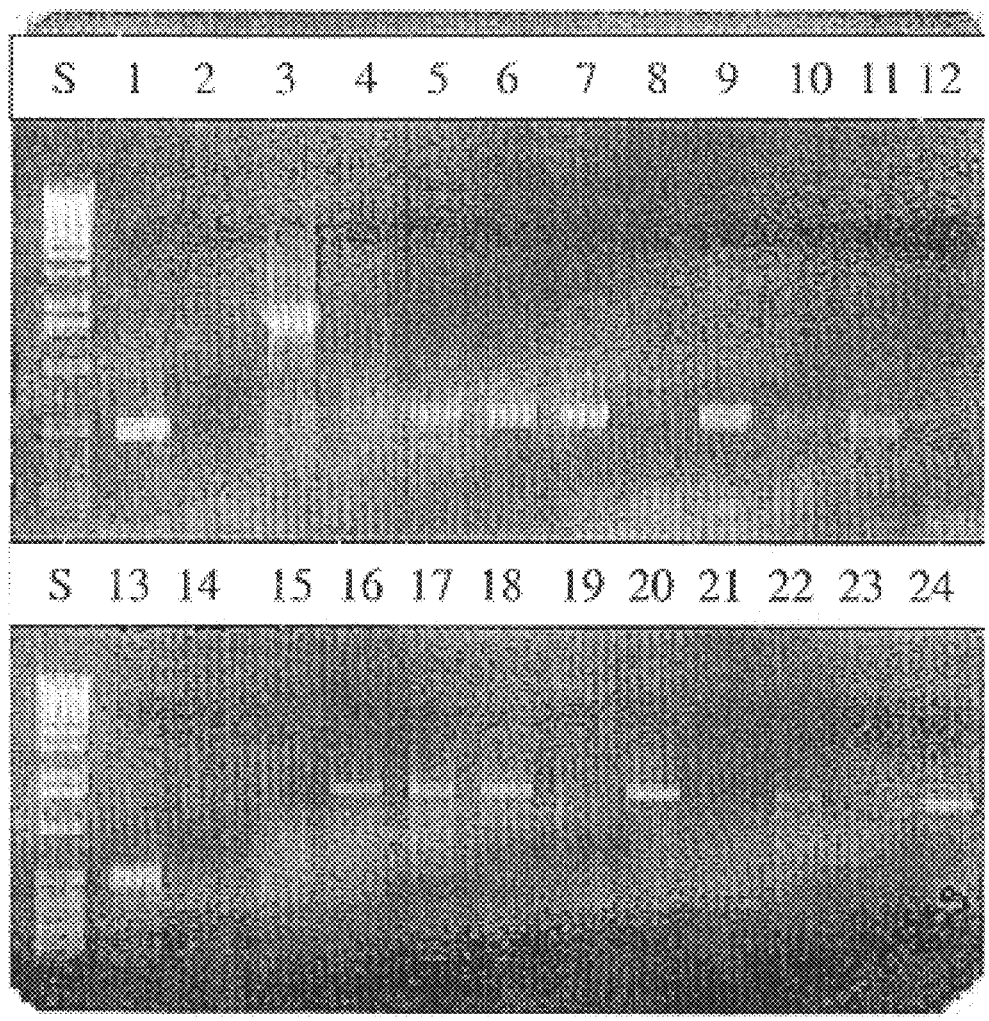
FIG. 5: PCR analysis of primary transformants. Loading sequence of the gel: S=bp standard, lane 1, 10 ng pCDUG+ (GAT1/GAT2 primers), lane 2, no DNA template, lane 3, 10 ng pCDUG+(CA6/P7 primers), lane 4, control sample 1WH23 (GAT1/GAT2 primers), lanes 5–14, samples 4WH21, 5WH 22, 6WH23, 7WH26, 8WH32, 9WH21, 10WH23, 11WH26, 12WH23, 13WH26, (GAT1/GAT2 primers), lane 15, control sample 1WH23 (CA6/P7 primers), lanes 16–24, samples 4WH21, 5WH 22, 6WH23, 7WH26, 8WH32, 9WH21, 10WH23, 11WH26, 12WH23, (CA6/P7 primers).

Plant samples were considered as positive, when the correct DNA bands were produced when tested with at least two primer combinations (FIG. 5).

Example 5

Production of Conditionally Male-sterile Wheat Plants Comprising a Herbicide Resistance Gene.

A plasmid for transformation of wheat plant cells is constructed by assembling the following well-known DNA fragments:

a marker gene cassette comprising the Ubiquitin promoter from maize containing its first exon and first intron, linked to the 5' untranslated leader sequence of the cab22 gene from pea, operably linked to the gentamycin acetyltransferase (GAT) coding sequence with the 3' untranslated region from the CaMV 35S transcript.

This cassette is flanked by frt1/frt2 sequences as part of the flp/frt excision system (Lyznik et al., 1993, above)

a deac gene expression cassette comprising the tapetum-specific promoter CA55 from maize (WO 92/13956) operably linked to the deac coding sequence (WO 98/27201) with the 3' untranslated region from the CaMV 35S transcript.

a chimeric sequence comprising the phenmedipham hydrolase (pmph) coding sequence (Streber et al. Plant Mol. Biol. 25:977–987; U.S. Pat. No. 5,347,047; U.S. Pat. No. 5,543,306) as a herbicide resistance marker under control of the constitutive 35S promoter from Cauliflower Mosaic Virus (Franck A. et al., Cell 21:285–294, 1980; Pietrzak M. et al., Nucl. Acids Res. 4:5857–5868, 1986).

Alternatively, the chimeric sequence contains a gene conferring glyphosate resistance (such as the EPSPS gene as described in, for example, U.S. Pat. No. 5,510,471) as a herbicide resistance marker, under control of a constitutive promoter (such as the 35S promoter from Cauliflower Mosaic Virus, or the ubiquitin promoter from Maize).

The complete insert is flanked by left and right T-DNA border sequences from plasmid pTIT37 of Agrobacterium tumefaciens (Caplan et al., 1983, above; Depicker et al. 1982, above).

The construct also contains the frt-excision sites of the flp/frt kick-out system, which allows for an optional excision of the marker gene by a recombinase. On the other hand the herbicide resistance marker can be maintained in the male-sterile line, in order to eliminate the pollinator plants by herbicide treatment on the production field under mixed planting conditions.

Primary transformants (T0) are tested for correct transformation by PCR and Southern blot analysis. T0 plants are screened for deacetylase activity as described above to identify positive transformation events and are tested for tolerance to the herbicide (phenmedipham or glyphosate). T0 plants are then selfed for the production of T1 progeny and developed as described above, whereby successive generations are tested for tolerance to the herbicide.

Example 6

Production of Hybrid Seed of Wheat Using Conditionally Male-sterile Plants

Conditional male sterility can be used in wheat breeding according to the following schemes.

a) Production of Composite Hybrid Seed

Seed comprising the deac gene under control of a stamen-selective promoter is obtained as described in example 1–4 above and is interplanted with wild-type plants (male parent) at a ratio which ensures adequate pollen transfer with a minimum of male parent plants (e.g., 80:20). Fields are sprayed with N-acetyl-PPT to induce male-sterility in the conditionally male-sterile plants. Seed harvested from the field optimally comprises about 80% hybrid seed (harvested from the conditionally male-sterile plants) and at least 20% selfed seed (harvested from the male parent).

b) Production of Pure Hybrid Seed

Plants are obtained according to the principles of example 5 above, whereby a herbicide resistance gene is introduced together with the deac gene. Seeds comprising this construct are planted in a mixture with seeds of a wheat inbred line as male parent (polinator), that are not resistant to the herbicide, at a ratio which ensures adequate pollen transfer with a minimum of male parent plants (e.g., 80:20). Fields are sprayed with N-acetyl-PPT to induce male-sterility in the conditionally male-sterile plants. After pollination, fields are sprayed with the herbicide to remove the male parent plants. Seed harvested from the field is pure (about 100%) hybrid seed.

c) Production of Pure Hybrid Seed Using Conditionally Female Sterile Plants

Seed capable of growing into conditionally male-sterile plants are obtained according to examples 1–4. Additionally, seeds capable of growing into conditionally female-sterile plants are obtained according to WO 98/13504. Seeds comprising the gene for conditional male sterility (female parent) are planted in a mixture with seeds of a homozygous inbred line comprising the gene for conditional female sterility (male parent or polinator) at a ratio which ensures adequate pollen transfer with a minimum of male parent plants (e.g., 80:20). Fields are sprayed with N-acetyl-PPT to induce male-sterility in the conditionally male-sterile plants and female-sterility in the conditionally female-sterile plants. Seed harvested from the field is pure hybrid seed (about 100%).

d) Production of Pure Hybrid Seed Using Female Sterile Plants

Seed capable of growing into conditionally male-sterile plants are obtained according to examples 1–4. These are planted in a mixture with seeds capable of growing into plants which are male fertile (male parent) but female-sterile (obtained either through inbreeding or by use of a transgene as described in U.S. Pat. No. 5,663,441 or U.S. Pat. No. 5,767,374) at a ratio which ensures adequate pollen transfer with a minimum of male parent plants (e.g., 80:20). Fields are sprayed with N-acetyl-PPT to induce male-sterility in the conditionally male-sterile plants. Seed harvested from the field is real hybrid seed (about 100%).

The above description of the invention is intended to be illustrative and not limiting. Various changes or modifications in the embodiments described may occur to those skilled in the art. These can be made without departing from the spirit or scope of the invention.

We claim:

1. A wheat plant, having a chimeric gene integrated into its genome, the chimeric gene comprising:
   a) a DNA molecule encoding a deacetylase from Stenotrophomonas sp; and
   b) a promoter directing stamen-selective expression in wheat wherein the DNA molecule encoding the deacetylase is in the same transcriptional unit and under control of the stamen-selective promoter.

2. The wheat plant of claim 1, wherein said DNA molecule encodes a biologically active fragment or a variant of the deacetylase encoded by SEQ ID No. 9.

3. The wheat plant of claim 1, wherein said DNA molecule encodes a deacetylase having the amino acid sequence of SEQ ID No. 8.

4. The wheat plant of claim 1, wherein said DNA molecule comprises the sequence of SEQ ID No. 9, or a sequence capable of hybridizing to SEQ ID No. 9 under standard stringent conditions.

5. The wheat plant of claim 1, wherein said stamen-selective promoter is a CA55 promoter.

6. The wheat plant of claim 1, wherein said stamen-selective promoter is a T72 promoter.

7. The wheat plant of claim 1, wherein said stamen-selective promoter is an E1 promoter.

8. A process for producing hybrid wheat seed, said process comprising
   i) producing seeds capable of growing into conditionally male-sterile wheat plants, said seeds having a chimeric gene integrated in their genome, the chimeric gene comprising:
      a) a DNA molecule encoding a deacetylase from Stenotrophomonas sp., and
      b) a stamen-selective promoter wherein the DNA molecule encoding the deacetylase is in the same transcriptional unit and under the control of the stamen-selective promoter;
   ii) interplanting said seeds capable of growing into conditionally male-sterile wheat plants with seeds capable of growing into male fertile wheat plants;
   iii) inducing male-sterility in said conditionally male-sterile plants by applying an N-acetyl-PPT, which in itself is not toxic to the plants or plant cells; and
   iv) harvesting hybrid seed.

9. The process of claim 8, wherein said DNA molecule encodes a biologically active fragment or a variant of the deacetylase encoded by SEQ. ID. No. 9.

10. The process of claim 8, wherein said DNA molecule encodes the deacetylase comprising the amino acid sequence of SEQ ID No. 8.

11. The process of claim 8, wherein said DNA molecule comprises the sequence of SEQ ID No. 9, or a sequence capable of hybridizing to SEQ ID No. 9 under standard stringent conditions.

12. The process of claim 8, wherein said stamen-selective promoter is a CA55 promoter.

13. The process of claim 8, wherein said stamen-selective promoter is a T72 promoter.

14. The process of claim 8, wherein said stamen-selective promoter is an E1 promoter.

15. The process of claim 8, wherein said male fertile plants are female-sterile.

16. A process for producing a conditionally male-sterile wheat plant, said process comprising
   i) transforming a wheat plant cell or tissue with a chimeric gene which comprises:
      a) a DNA molecule encoding a deacetylase from Stenotrophomonas sp., and
      b) a stamen-selective promoter wherein the DNA molecule encoding the deacetylase is in the same transcriptional unit and under the control of said stamen-selective promoter;
   ii) regenerating said conditionally male-sterile plant from said cell or tissue; and optionally, iii) applying an N-acetyl-PPT to said conditionally male-sterile plant, which is in itself not toxic to the plant or plant cells to make said plant male-sterile.

17. The process of claim 16, wherein said DNA molecule encodes a biologically active fragment of the deacetylase encoded by SEQ. ID. No. 9.

18. The process of claim 16, wherein said DNA molecule encodes the deacetylase of SEQ ID No. 8.

19. The process of claim 16, wherein said DNA molecule comprises the sequence of SEQ ID No. 9, or a sequence capable of hybridizing to SEQ ID No. 9 under standard stringent conditions.

20. The process of claim 16, wherein said stamen-selective promoter is a CA55 promoter.

21. The process of claim 16, wherein said stamen-selective promoter is a T72 promoter.

22. The process of claim 16, wherein said stamen-selective promoter is an E1 promoter.

23. A conditionally male sterile wheat plant obtained by the process of claim 16.

24. A process for generating male sterility in wheat plants, said process comprising i) obtaining a conditionally male-sterile wheat plant by transforming a wheat plant cell or tissue with a chimeric gene which comprises:
   a) a DNA molecule encoding a deacetylase from Stenotrophomonas sp., and
   b) a stamen-selective promoter wherein the DNA molecule encoding the deacetylase is in the same transcriptional unit and under the control of said stamen-selective promoter, and regenerating said conditionally male-sterile plant from said cell or tissue; and optionally obtaining conditionally male-sterile progeny from said plant ii) applying an N-acetyl-PPT to said conditionally male-sterile plant or its conditionally male-sterile progeny, which is in itself not toxic to the plant or plant cells to make said plant male-sterile.

25. A male sterile wheat plant, or cells or tissues thereof, obtained by the process of 24.

26. Wheat plant cells, tissues or seed, each transformed with the chimeric DNA of claim 1.

* * * * *

SEQUENCE LISTING

```
<160> NUMBER OF SEQ ID NOS: 9

<210> SEQ ID NO 1
<211> LENGTH: 6217
<212> TYPE: DNA
<213> ORGANISM: Artificial Sequence
<220> FEATURE:
<223> OTHER INFORMATION: Description of Artificial  Sequence: NotI
      cassette from plasmid pCDUG
<220> FEATURE:
<221> NAME/KEY: misc_feature
<222> LOCATION: (9)..(36)
<223> OTHER INFORMATION: Left border from pTiT3 7
<220> FEATURE:
<221> NAME/KEY: promoter
<222> LOCATION: (116)..(1020)
<223> OTHER INFORMATION: ubiquitin promoter from maize
<220> FEATURE:
<221> NAME/KEY: exon
<222> LOCATION: (1021)..(1101)
<223> OTHER INFORMATION: 1. exon of ubiquitin gene
<220> FEATURE:
<221> NAME/KEY: intron
<222> LOCATION: (1102)..(2111)
<223> OTHER INFORMATION: 1. exon of ubiquitin gene
<220> FEATURE:
<221> NAME/KEY: enhancer
<222> LOCATION: (2133)..(2199)
<223> OTHER INFORMATION: translational enhancer fr om cab22 gene
<220> FEATURE:
<221> NAME/KEY: gene
<222> LOCATION: (2201)..(2812)
<223> OTHER INFORMATION: gentamycin acetyltransferase  gene
<220> FEATURE:
<221> NAME/KEY: terminator
<222> LOCATION: (2815)..(3049)
<223> OTHER INFORMATION: terminator from 35S RN A gene
<220> FEATURE:
<221> NAME/KEY: promoter
```

```
<222> LOCATION: (3071)..(4248)
<223> OTHER INFORMATION: ca55 promoter
<220> FEATURE:
<221> NAME/KEY: gene
<222> LOCATION: (4261)..(5625)
<223> OTHER INFORMATION: Deacetylase gene
<220> FEATURE:
<221> NAME/KEY: terminator
<222> LOCATION: (5646)..(5841)
<223> OTHER INFORMATION: terminator from 35S RN A gene
<220> FEATURE:
<221> NAME/KEY: misc_feature
<222> LOCATION: (6094)..(6118)
<223> OTHER INFORMATION: Right border from pTiT 37

<400> SEQUENCE: 1
```

| | | | | | |
|---|---|---|---|---|---|
| ggccgcgctg | gtggcaggat | atattgtggt | gtaaavaaat | tcctgcaggc a | attggtacc      60 |
| tacgtatgca | tggcgcgcca | tatgcccaat | tcgagctcgg | tacccccgcgc c | ataccctgca    120 |
| gtgcagcgtg | acccggtcgt | gccctctct  | agagataatg | agcattgcat g | tctaagtta     180 |
| taaaaaatta | ccacatattt | tttttgtcac | acttgtttga | agtgcagttt a | tctatcttt     240 |
| atacatatat | ttaaactta  | ctctacgaat | aatataatct | atagtactac a | ataatatca     300 |
| gtgttttaga | gaatcatata | aatgaacagt | tagacatggt | ctaaaggaca a | ttgagtatt     360 |
| ttgacaacag | gactctacag | ttttatcttt | ttagtgtgca | tgtgttctcc t | tttttttg      420 |
| caaatagctt | cacctatata | atacttcatc | cattttatta | gtacatccat t | tagggttta     480 |
| gggttaatgg | tttttataga | ctaatttttt | tagtacatct | atttttattct a | ttttagcct     540 |
| ctaaattaag | aaaactaaaa | ctctatttta | gttttttat  | ttaataatttt a | gatataaaa     600 |
| tagaataaaa | taaagtgact | aaaaattaaa | caaatacct  | ttaagaaatt a | aaaaaacta     660 |
| aggaaacatt | tttcttgttt | cgagtagata | atgccagcct | gttaaacgcc g | tcgatcgac     720 |
| gagtctaacg | gacaccaacc | agcgaaccag | cagcgtcgcg | tcgggccaag c | gaagcagac     780 |
| ggcacggcat | ctctgtcgct | gcctctggac | ccctctcgag | agttccgctc c | accgttgga     840 |
| cttgctccgc | tgtcggcatc | cagaaattgc | gtggcggagc | ggcagacgtg a | gccggcacg     900 |
| gcaggcggcc | tcctcctcct | ctcacggcac | ggcagctacg | ggggattcct t | tcccaccgc     960 |
| tccttcgctt | tccctttcctc | gcccgccgta | ataaatagac | acccccgcca c | accctctttt   1020 |
| ccccaacctc | gtgttgttcg | gagcgcacac | acacacaacc | agatctcccc c | aaatccacc    1080 |
| cgtcggcacc | tccgcttcaa | ggtacgccgc | tcgtcctccc | ccccccccc t | ctctacctt    1140 |
| ctctagatcg | gcgttccggt | ccatggttag | ggcccggtag | ttctacttct g | ttcatgtttt   1200 |
| gtgttagatc | cgtgtttgtg | ttagatccgt | gctgctagcg | ttcgtacacg g | atgcgacct    1260 |
| gtacgtcaga | cacgttctga | ttgctaactt | gccagtgttt | ctctttgggg a | atcctggga    1320 |
| tggctctagc | cgttccgcag | acgggatcga | tttcatgatt | tttttttgttt c | gttgcatag    1380 |
| ggtttggttt | gcccttttcc | tttatttcaa | tatatgccgt | gcacttgttt g | tcgggtcat    1440 |
| cttttcatgc | tttttttttgt | cttggttgtg | atgatgtggt | ctggttgggc g | gtcgttcta    1500 |
| gatcggagta | gaattctgtt | tcaaactacc | tggtggattt | attaattttg g | atctgtatg    1560 |
| tgtgtgccat | acatattcat | agttacgaat | tgaagatgat | ggatggaaat a | tcgatctag    1620 |
| gataggtata | catgttgatg | cgggttttac | tgatgcatat | acagagatgc t | ttttgttcg    1680 |
| cttggttgtg | atgatgtggt | gtggttgggc | ggtcgttcat | tcgttctaga t | cggagtaga    1740 |
| atactgtttc | aaactacctg | gtgtatttat | taatttggga | actgtatgtg t | gtgtcatac    1800 |
| atcttcatag | ttacgagttt | aagatggatg | gaaatatcga | tctaggatag g | tatacatgt    1860 |

-continued

```
tgatgtgggt tttactgatg catatacatg atggcatatg cagcatctat t catatgctc    1920
taaccttgag tacctatcta ttataataaa caagtatgtt ttataattat t ttgatcttg    1980
atatacttgg atgatggcat atgcagcagc tatatgtgga ttttttttagc c ctgccttca    2040
tacgctattt atttgcttgg tactgtttct tttgtcgatg ctcaccctgt t gtttggtgt    2100
tacttctgca ggtcgactct agaggatctc gtcgagctca tttctctatt a cttcagcca    2160
taacaaaaga actcttttct cttcttatta aaccaaaacc atggatccga g tattcaaca    2220
tttccaaaca aagttaggca tcacaaagta cagcatcgtg accaacagca c cgattccgt    2280
cacactgcgc ctcatgactg agcatgacct tgcgatgctc tatgagtggc t aaatcgatc    2340
tcatatcgtc gagtggtggg gcggagaaga agcacgcccg acacttgctg a cgtacagga    2400
acagtacttg ccaagcgttt tagcgcaaga gtccgtcact ccatacattg c aatgctgaa    2460
tggagagccg attgggtatg cccagtcgta cgttgctctt ggaagcgggg a cggatggtg    2520
ggaagaagaa accgatccag gagtacgcgg aatagaccag tcactggcga a tgcatcaca    2580
actgggcaaa ggcttgggaa ccaagctggt tcgagctctg gttgagttgc t gttcaatga    2640
tcccgaggtc accaagatcc aaacggaccc gtcgccgagc aacttgcgag c gatcccatg    2700
ctacgagaaa gcggggtttg agaggcaagg taccgtaacc accccagatg g tccagccgt    2760
gtacatggtt caaacacgcc aggcattcga gcgaacacgc agtgatgcct g aggctagca    2820
agcttggaca cgctgaaatc accagtctct ctctacaaat ctatctctct c tattttctc    2880
cataataatg tgtgagtagt tcccagataa gggaattagg gttcctatag g gtttcgctc    2940
atgtgttgag catataagaa acccttagta tgtatttgta tttgtaaaat a cttctatca    3000
ataaaatttc taattcctaa aaccaaaatc cagtactaaa atccagatca t gcatggtac    3060
agcggccggg tggtatgcat caatagagcc ggaagatggt ctggagtaag g acctggcag    3120
tgtgatacgg gaacttgaca tctgaataga tattctccct tgtccctctg g taaaaaaaa    3180
ctgttgtcac atttgccttc gctgtgactt ggatgtatca tgtatatctt t gaccattga    3240
tatcttggtt aatcagaccg tgcattacaa tcatggcctc attcatatag g gtttagggt    3300
taccacgatt ggtttgcata agtagtaccc ctccgtttca aattatgtcg t attttgatt    3360
ttttagatac acttttttata taatttttta ttttaaatta ggtgttttat a taatacgta    3420
tctaagtgta taataaaata tatgtatcta aaagctgtaa tttagtataa a ttagaatgg    3480
tgtatatctt caatgtatga caaataattt gaaatggagg agggtatgaa a agccaaaac    3540
ctcctagaat atggaatgga gggaatacat acaaattctt tgcttcagtt a aaagaaacg    3600
agaaaggag gggaatgggg aatcgtactt cagtttttac gagttttcat c aaacatgta    3660
tgcacgtctt cccttggttg atgcatcttt ttggcaaatc ttcgtttaat t gcggcttct    3720
tttttatacc gttcgaaggt tttcgtcgtc aatgctgaaa ctccactttc a ccaccttcg    3780
gttgcatctg cttgctttca attcacctct aattagtcca agtgtttcat t ggacgaagg    3840
tccaagtcct tcagatcatc tcaattttct ttgatctgaa acaacaattt a aaactgatt    3900
ttgttacctt gacctgtcga agaccttcga acgaacggta ctgtaaaaat a ctgtacctc    3960
agatttgtga tttcaattcg attcgggtct cctggctgga tgaaaccaat g cgagagaag    4020
aagaaaaaat gttgcattac gctcactcga tcggttacga gcacgtagtt g gcgcctgtc    4080
acccaaccaa accagtagtt gaggcacgcc ctgtttgctc acgatcacga a cgtacagca    4140
ctataaaaca cgcagggact ggaaagcgag atttcacagc tcaaagcagc c aaaacgcag    4200
aagctgcact gcatatacag aagatacatc gagctaacta gctgcagcgg a tccttgagg    4260
```

-continued

```
atgatccgca agaccgttct gttgactgcg ctgtcctgcg ccctggcctc c gcgacagcc      4320 accgccgccg aaggccagcg gcccgaggtg gaggccgccg ccgcgcgcct g cagcggcag      4380 gtggtggagt ggcgccgcga tttccaccag catccggagc tgtccaaccg c gaggtgcgc      4440 accgccgcca aggtggccga gcgcctgcgc gcgatgggcc tgcaaccgca g accggcgtc      4500 gccgtgcacg gcgtggtggc gatcatcaag gcgccctgc cggggccgaa g atcgccctg      4560 cgcgcggaca tggacgcgct gccggtgacc gaacagaccg gctgccgtt c gcctccacc      4620 gccacggccg agtaccgcgg cgagaaggtc ggggtgatgc atgcctgcgg c cacgacgcc      4680 cataccgcca ccctgctcgg cgtggccgac gcgctggtgg ccatgcgcga c acgctgccc      4740 ggcgaagtaa tgctgatctt ccagccggcc gaggaaggcg cgccgccgcc g gagcagggc      4800 ggtgccgagc tgatgctcaa ggaggggctg ttcaaggagt tcaagccgga g gcggtgttc      4860 ggcctgcacg tgttctccag cgtccaggcc gggcagatcg ccgtgcgcgg c ggcccgctg      4920 atggccgcct ccgaccgctt cgccatcacc gtcaacggcc gccagaccca t ggctcggcg      4980 ccctggaacg gcatcgatcc gattgtcgcc gcctccgacc tgatcggcac c gcgcagacc      5040 atcgtcagcc gccgcgccaa cctgtccaag cagccggcgg tgctgacctt c ggcgcgatc      5100 aagggcggca tccgctacaa catcatcccc gactcggtgg agatggtcgg c accatccgc      5160 accttcgacc cggacatgcg caagcagatc ttcgccgact tgcgcaacgt c gccgagcac      5220 accgctgccc catggcgcca ccgccaccac cgacatctac gagaaggacg g caacccggc      5280 cacggtcaac gacccggcgc tgaccgcgcg catgctgccc agcctgcagg c cgtggtcgg      5340 caaggacaac gtctacgagc cgccgctgca gatgggctcg gaggacttct c gctgtatgc      5400 gcagcaggtg ccggcgatgt tcttcttcgt cggctccacc ggcgcgggca t cgacccggc      5460 caccgcgccc agcaaccact cgccgaagtt cctgctcgac gagaaggcgc t ggacgtggg      5520 cctgcgcgcg ctgctgcagg tgtcgctgga ctatctgcac ggtggcaagg c ggggtgacc      5580 cctgccagta tcgtgccccc gatacggaag aaggacctcc catgagcgtc g acctgcagg      5640 catgccgctg aaatcaccag tctctctcta caaatctatc tctctctata a taatgtgtg      5700 agtagttccc agataaggga attagggttc ttatagggtt tcgctcatgt g ttgagcata      5760 taagaaaccc ttagtatgta tttgtatttg taaaatactt ctatcaataa a atttctaat      5820 tcctaaaacc aaaatccagt ggcgagctcg aattgggccc tgtacagcgg c cggccgcgt      5880 taacgcgtat actctagagc gatcgcaggc ttgcttttcc attattttgc g caacaagtc      5940 acggatattc gtgaaaacga caaaaactgc gaaatttgcg ggcagtgcct t cagttttcc      6000 tattaatatt tagtttgaca ccagttgcta tcattgcggc caagctcagg a tcagattgt      6060 cgtttcccgc cttcggttta aactatcagt gtttgacagg atatattggc g ggtaaacct      6120 aagagaaaag agcgtttatt agaataatcg gatatttaaa agggcgtgaa a aggtttatc      6180 cgttcgtcca tttgtatgtg catgcaagct agcggcc                              6217
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer GAT1

<400> SEQUENCE: 2
gcaccgattc cgtcacactg c                                                21

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial  Sequence: primer GAT2

<400> SEQUENCE: 3
gtacacggct ggaccatctg g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial  Sequence: primer CA6

<400> SEQUENCE: 4
gttacgagca cgtagttggc g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial  Sequence: primer 7PA

<400> SEQUENCE: 5
gctcatggga ggtccttctt c                                              21

<210> SEQ ID NO 6
<211> LENGTH: 32
<212> TYPE: DNA
<213> ORGANISM: Artificial Sequence
<220> FEATURE:
<223> OTHER INFORMATION: Description of Artificial  Sequence: primer CA1

<400> SEQUENCE: 6
tacgccccgg gtggtatgca tcaatagagc cg                                  32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial  Sequence: primer CA2

<400> SEQUENCE: 7
tacgcggatc cgctgcagct agttagctcg at                                  32

<210> SEQ ID NO 8
<211> LENGTH: 454
<212> TYPE: PRT
<213> ORGANISM: Stenotrophomonas sp.

<400> SEQUENCE: 8
```

Met Ile Arg Lys Thr Val Leu Leu Thr Ala L eu Ser Cys Ala Leu Ala
 1               5                  10                  15

Ser Ala Thr Ala Thr Ala Ala Glu Gly Gln A rg Pro Glu Val Glu Ala
            20                  25                  30

Ala Ala Ala Arg Leu Gln Arg Gln Val Val G lu Trp Arg Arg Asp Phe
        35                  40                  45

His Gln His Pro Glu Leu Ser Asn Arg Glu V al Arg Thr Ala Ala Lys
    50                  55                  60

```
Val Ala Glu Arg Leu Arg Ala Met Gly Leu Gln Pro Gln Thr Gly Val
 65                  70                  75                  80

Ala Val His Gly Val Val Ala Ile Ile Lys Gly Ala Leu Pro Gly Pro
                 85                  90                  95

Lys Ile Ala Leu Arg Ala Asp Met Asp Ala Leu Pro Val Thr Glu Gln
            100                 105                 110

Thr Gly Leu Pro Phe Ala Ser Thr Ala Thr Ala Glu Tyr Arg Gly Glu
        115                 120                 125

Lys Val Gly Val Met His Ala Cys Gly His Asp Ala His Thr Ala Thr
130                 135                 140

Leu Leu Gly Val Ala Asp Ala Leu Val Ala Met Arg Asp Thr Leu Pro
145                 150                 155                 160

Gly Glu Val Met Leu Ile Phe Gln Pro Ala Glu Gly Ala Pro Pro
                165                 170                 175

Pro Glu Gln Gly Gly Ala Glu Leu Met Leu Lys Gly Leu Phe Lys
            180                 185                 190

Glu Phe Lys Pro Glu Ala Val Phe Gly Leu His Val Phe Ser Ser Val
        195                 200                 205

Gln Ala Gly Gln Ile Ala Val Arg Gly Gly Pro Leu Met Ala Ala Ser
210                 215                 220

Asp Arg Phe Ala Ile Thr Val Asn Gly Arg Gln Thr His Gly Ser Ala
225                 230                 235                 240

Pro Trp Asn Gly Ile Asp Pro Ile Val Ala Ala Ser Asp Leu Ile Gly
                245                 250                 255

Thr Ala Gln Thr Ile Val Ser Arg Arg Ala Asn Leu Ser Lys Gln Pro
            260                 265                 270

Ala Val Leu Thr Phe Gly Ala Ile Lys Gly Gly Ile Arg Tyr Asn Ile
        275                 280                 285

Ile Pro Asp Ser Val Glu Met Val Gly Thr Ile Arg Thr Phe Asp Pro
290                 295                 300

Asp Met Arg Lys Gln Ile Phe Ala Asp Leu Arg Asn Val Ala Glu His
305                 310                 315                 320

Thr Ala Ala Ala Trp Arg His Arg His Arg His Leu Arg Glu Gly
                325                 330                 335

Arg Gln Pro Gly His Gly Gln Arg Pro Gly Ala Asp Arg Ala His Ala
            340                 345                 350

Ala Gln Pro Ala Arg Gly Arg Gln Gly Gln Arg Leu Arg Ala Ala
        355                 360                 365

Ala Ala Asp Gly Leu Gly Leu Leu Ala Val Cys Ala Ala Gly Ala
370                 375                 380

Gly Asp Val Leu Leu Arg Arg Leu His Arg Arg Gly His Arg Pro Gly
385                 390                 395                 400

His Arg Ala Gln Gln Pro Leu Ala Glu Val Pro Ala Arg Arg Glu Gly
                405                 410                 415

Ala Gly Arg Gly Pro Ala Arg Ala Ala Gly Val Ala Gly Leu Ser
            420                 425                 430

Ala Arg Trp Gln Gly Gly Val Thr Pro Ala Ser Ile Val Pro Pro Ile
        435                 440                 445

Arg Lys Lys Asp Leu Pro
450

<210> SEQ ID NO 9
<211> LENGTH: 3078
```

<212> TYPE: DNA
<213> ORGANISM: Artificial Sequence
<220> FEATURE:
<223> OTHER INFORMATION: Description of Artificial Sequence: deac gene cassette

<400> SEQUENCE: 9

```
tggtatgcat caatagagcc ggaagatggt ctggagtaag gacctggcag t gtgatacgg      60
gaacttgaca tctgaataga tattctccct tgtccctctg gtaaaaaaaa c tgttgtcac     120
atttgccttc gctgtgactt ggatgtatca tgtatatctt tgaccattga t atcttggtt    180
aatcagaccg tgcattacaa tcatggcctc attcatatag ggtttagggt t accacgatt    240
ggtttgcata agtagtaccc ctccgtttca aattatgtcg tattttgatt t tttagatac    300
acttttata taattttttta ttttaaatta ggtgttttat ataatacgta t ctaagtgta    360
taataaaata tatgtatcta aaagctgtaa tttagtataa attagaatgg t gtatatctt    420
caatgtatga caaataattt gaaatggagg agggtatgaa aagccaaaac c tcctagaat    480
atggaatgga gggaatacat acaaattctt tgcttcagtt aaaagaaacg a gaaaaggag    540
gggaatgggg aatcgtactt cagtttttac gagttttcat caaacatgta t gcacgtctt    600
cccttggttg atgcatcttt ttggcaaatc ttcgtttaat tgcggcttct t ttttatacc    660
gttcgaaggt tttcgtcgtc aatgctgaaa ctccactttc accaccttcg g ttgcatctg    720
cttgctttca attcacctct aattagtcca agtgtttcat tggacgaagg t ccaagtcct    780
tcagatcatc tcaattttct ttgatctgaa acaacaattt aaaactgatt t tgttacctt    840
gacctgtcga agaccttcga acgaacggta ctgtaaaaat actgtacctc a gatttgtga    900
tttcaattcg attcgggtct cctggctgga tgaaaccaat gcgagagaag a agaaaaaat    960
gttgcattac gctcactcga tcggttacga gcacgtagtt ggcgcctgtc a cccaaccaa   1020
accagtagtt gaggcacgcc ctgtttgctc acgatcacga acgtacagca c tataaaaca   1080
cgcagggact ggaaagcgag atttcacagc tcaaagcagc caaaacgcag a agctgcact   1140
gcatatacag aagatacatc gagctaacta gctgcagcgg atccttgagg a tgatccgca   1200
agaccgttct gttgactgcg ctgtcctgcg ccctggcctc cgcgacagcc a ccgccgccg   1260
aaggccagcg gcccgaggtg gaggccgccg ccgcgcgcct gcagcggcag g tggtggagt   1320
ggcgccgcga tttccaccag catccggagc tgtccaaccg cgaggtgcgc a ccgccgcca   1380
aggtggccga gcgcctgcgc gcgatgggcc tgcaaccgca gaccggcgtc g ccgtgcacg   1440
gcgtggtggc gatcatcaag ggcgccctgc cggggccgaa gatcgccctg c gcgcggaca   1500
tggacgcgct gccggtgacc gaacagaccg ggctgccgtt cgcctccacc g ccacggccg   1560
agtaccgcgg cgagaaggtc gggtgatgc atgcctgcgg ccacgacgcc c ataccgcca   1620
ccctgctcgg cgtggccgac gcgctggtgg ccatgcgcga cacgctgccc g gcgaagtaa   1680
tgctgatctt ccagccggcc gaggaaggcg cgccgccgcc ggagcagggc g gtgccgagc   1740
tgatgctcaa ggagggctg ttcaaggagt tcaagccgga ggcggtgttc g gcctgcacg   1800
tgttctccag cgtccaggcc gggcagatcg ccgtgcgcgg cggcccgctg a tggccgcct   1860
ccgaccgctt cgccatcacc gtcaacggcc gccagaccca tggctcggcg c cctggaacg   1920
gcatcgatcc gattgtcgcc gcctccgacc tgatcggcac cgcgcagacc a tcgtcagcc   1980
gccgcgccaa cctgtccaag cagcggcgg tgctgacctt cggcgcgatc a agggcggca   2040
tccgctacaa catcatcccc gactcggtgg agatggtcgg caccatccgc a ccttcgacc   2100
cggacatgcg caagcagatc ttcgccgact gcgcaacgt cgccgagcac a ccgctgccg   2160
```

```
catggcgcca ccgccaccac cgacatctac gagaaggacg gcaacccggc c acggtcaac   2220 gacccggcgc tgaccgcgcg catgctgccc agcctgcagg ccgtggtcgg c aaggacaac   2280 gtctacgagc cgccgctgca gatgggctcg gaggacttct cgctgtatgc g cagcaggtg   2340 ccggcgatgt tcttcttcgt cggctccacc ggcgcgggca tcgacccggc c accgcgccc   2400 agcaaccact cgccgaagtt cctgctcgac gagaaggcgc tggacgtggg c ctgcgcgcg   2460 ctgctgcagg tgtcgctgga ctatctgcac ggtggcaagg cggggtgacc c ctgccagta   2520 tcgtgccccc gatacggaag aaggacctcc catgagcgtc gacctgcagg c atgccgctg   2580 aaatcaccag tctctctcta caaatctatc tctctctata ataatgtgtg a gtagttccc   2640 agataaggga attagggttc ttatagggtt tcgctcatgt gttgagcata t aagaaaccc   2700 ttagtatgta tttgtatttg taaaatactt ctatcaataa aatttctaat t cctaaaacc   2760 aaaatccagt ggcgagctcg aattgggccc tgtacagcgg ccggccgcgt t aacgcgtat   2820 actctagagc gatcgcaggc ttgcttttcc attattttgc gcaacaagtc a cggatattc   2880 gtgaaaacga caaaaactgc gaaatttgcg ggcagtgcct tcagttttcc t attaatatt   2940 tagtttgaca ccagttgcta tcattgcggc caagctcagg atcagattgt c gtttcccgc   3000 cttcggttta aactatcagt gtttgacagg atatattggc gggtaaacct a agagaaaag   3060 agcgtttatt agaataat                                                   3078
```